Figure 1:
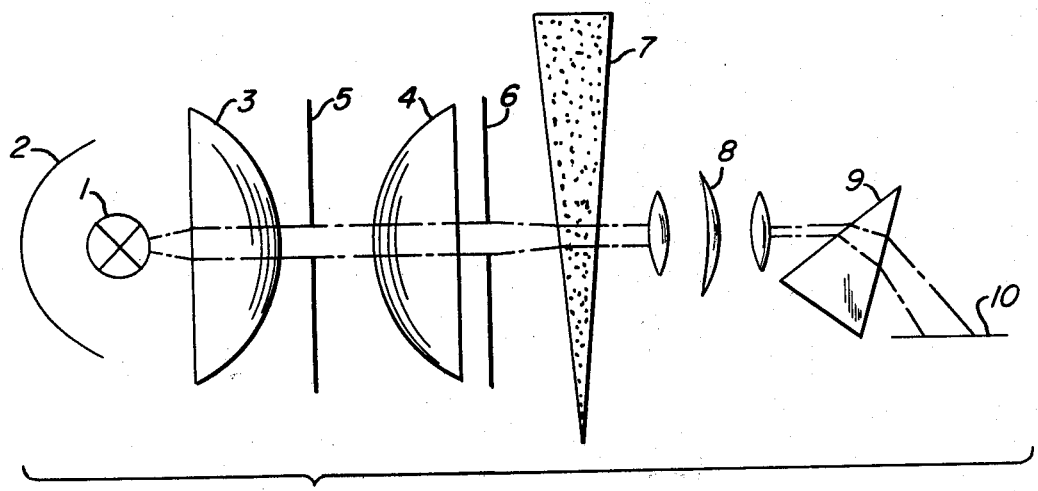

United States Patent [19]

Eidenschink et al.

[11] 4,274,740

[45] Jun. 23, 1981

[54] OPTICAL PROCESS AND APPARATUS FOR DETERMINING PARTICLE SIZE OF COLLOIDAL SOLUTION

[76] Inventors: Herrn H. Eidenschink; Marianne Eidenschink, both of Gutenbergstr. 1, 5609 Huckeswagen, Fed. Rep. of Germany

[21] Appl. No.: 59,081

[22] Filed: Jul. 19, 1979

[30] Foreign Application Priority Data

Jul. 21, 1978 [DE] Fed. Rep. of Germany ....... 2832091

[51] Int. Cl.³ .......................................... G01N 15/02
[52] U.S. Cl. .................................................. 356/336
[58] Field of Search .............................. 356/335, 336; 250/222 PC, 574

[56] References Cited

PUBLICATIONS

Barrow, Gordon M., *Physical Chemistry*, McGraw-Hill, New York, 1961, pp. 662-669.

*Primary Examiner*—John K. Corbin
*Assistant Examiner*—Bruce Y. Arnold
*Attorney, Agent, or Firm*—Thomas H. Murray; Clifford A. Poff

[57] ABSTRACT

Method and apparatus for determining the colloid size of particles in a colloidal solution include the use of a wedge-shaped container for a sample of the colloidal solution. The container is moved in the direction of the wedge shape perpendicular to the path of a light beam to produce a measured sample thickness of the colloidal solution. Due to the Tyndall effect, the measured sample thickness is a function of the scattering of the light beam. A lens arranged between the sample holder and a dispersion prism directs the beam of light emerging from the sample holder to the prism for dispersion and impingement upon an image screen. The sample holder is moved until only red light appears on the image screen. The thickness of the light path through the sample is measured and the particle size is computed according to an equation.

10 Claims, 2 Drawing Figures

U.S. Patent  Jun. 23, 1981  4,274,740

OPTICAL PROCESS AND APPARATUS FOR DETERMINING PARTICLE SIZE OF COLLOIDAL SOLUTION

BACKGROUND OF THE INVENTION

This invention relates to a method and apparatus for optical determination of the particle size of a colloidal solution, especially dispersions of synthetic resins, wherein the invention utilizes the scattering of a light beam by the Tyndall effect upon passing through a sample of the colloidal solution.

Various methods are known in the art for determining the size of the particles in a synthetic resin dispersion. One known method is based on a statistical evaluation of photographs produced by the use of an electron microscope. In other known methods, the size of particles in a colloidal dispersion is determined from the dependent angle and/or the wavelength of the scattered light within the collidal dispersion. It is also known in the art to evaluate the radius of a particle in a colloidal dispersion by the statistical evaluation of the Brownian movement of molecules as a function of the radius of the particle. It is a further known practice to use turbidity measurements for determining the particle size in the colloidal dispersion. The results obtainable from turbidity measurements are too inaccurate. Other known measurement procedures have the disadvantage that disproportionately large amounts of equipment and operating time are required to carry out the measurements.

In general, dispersions occur in polydispersed form and the mean particle size is of primary interest. In addition, the particle size distribution is, in many cases, of interest. In recent years, manufacturers and particularly processors, have shown great interest in a rapid determination of the particle sizes of synthetic resin dispersion. That is because knowledge of the particle size provides a basis for conclusions as to the properties of the end product, e.g., a resulting layer of paint. On the other hand, manufacturers of dispersions of plastics have an immediate capability, through suitable procedures and additions, for obtaining desired particle sizes and particle size distributions in a dispersion. In this way, during the production of such dispersions, it is possible to meet the necessary stipulations for obtaining the desired properties in the end product. In the past, a measuring process used for these and other purposes lacked the ability to determine the particle size of synthetic resin dispersion with sufficient speed and accuracy. The present invention is addressed to providing a solution to the shortcomings of known measuring processes and apparatus.

SUMMARY OF THE INVENTION

It is an object of the present invention to provide a method and apparatus for determining the particle size of a colloidal solution, especially a synthetic resin dispersion, in a more efficient and effective manner through the dispersion of light by the Tyndall effect.

More particularly, according to the present invention, there is provided a method for determining the particle size of a colloidal solution, especially a synthetic resin dispersion, wherein the method includes the steps of providing a colloidal solution sample with a varying thickness, directing a light beam to pass through the colloidal solution sample in the direction normal to that of the varying thickness, dispersing the emerging light beam from the sample onto an image screen, establishing a measured colloidal solution sample section by relative displacement between the light beam and the varying thickness of the colloidal solution sample such that only the long-wave part of the visible spectrum of the dispersed light appears on the image screen, determining the length of the measured colloidal solution sample section, and determining the particle size of the colloidal solution in accordance with the formula:

$$r = \frac{1}{c \cdot d \cdot E_{(c)} \cdot n}$$

where
 $r$ = radius of the particle ($\mu$m),
 $c$ = concentration of the colloidal solution in volume %,
 $d$ = thickness of measured colloidal solution sample section (mm),
 $E_{(c)}$ = concentration factor at concentration c, and
 $n$ = a constant.

Thus, according to the invention, a light beam is directed to propagate through a sample of a colloidal solution within a container which provides a continuously changing layer thickness of solution. A measuring sample section is selected by relative displacement between the light beam and the thickness of the sample to vary the length of the light path through the sample. The light emerging from the sample is dispersed into a spectrum and projected onto an image screen. The measuring section is selected such that the projected dispersed light beam contains only the long-wave part or the red part of the visible spectrum; whereupon the set length of the measured section is measured and the particle size is determined in accordance with the aforesaid formula.

According to the preferred aspect of the present invention, the measuring section is advantageously established by moving a wedge-shaped sample of solution in the longitudinal direction of the wedge and perpendicular to the light beam.

The underlying concept of the invention is based on a determination of the length of the Tyndall cone which can be seen when a parallel concentrated light beam is passed through a dispersion. In order to calculate the particle size of the colloidal solution with the aid of the above formula, it is necessary to know the measured length of the measuring section and the concentration of the solution in volume percent. This concentration of the solution is a characteristic quantity usually supplied by the manufacturer along with a concentration factor which can be determined in a manner hereinafter set forth.

The present invention further provides a measuring apparatus to carry out the above-described method wherein the apparatus is characterized by the fact that a light source is provided to produce a light beam and a sequential arrangement of parts in the path of light emanating from the source includes a condenser to concentrate the light beam, a wedge-shaped movable sample holder or cell made of transparent material, an objective, a prism and an image screen.

Advantageously, the light beam is caused to pass through a condenser consisting of two plano-convex lenses between which a diaphragm stop is located. A second diaphragm stop is placed, if desired, between the condenser and the sample holder. The light source is placed at the focal point of a parabolic mirror.

The advantages obtained from the present invention reside in the fact that measurements employed to determine the particle size can be carried out rapidly with the aid of a portable and simple to manipulate measuring apparatus. These advantages also include obtaining sufficiently accurate results with dispersions having particles sizes in the range of 0.01 to 5 μm. By contrast with previously-known methods, the method of the present invention is characterized as a fast method for determining the particle size of a colloidal solution which can be readily carried out, after suitable instructions, by untrained personnel.

Figure 2:
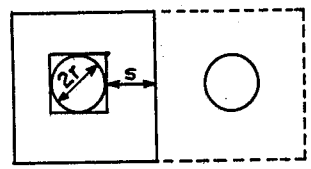

These features and advantages of the present invention as well as others will be more fully understood when the following description is read in light of the accompanying drawing, in which:

FIG. 1 illustrates the arrangement of parts forming the preferred form of measuring apparatus which is also useful to carry out the method of the present invention; and FIG. 2 is a diagram used in the accompanying description to set forth the computation to derive the concentration factor of a colloidal solution.

The apparatus illustrated in FIG. 1 includes a light source 1 arranged at the focal point of a parabolic mirror 2. The emerging beam of light passes in sequence through a first plano-convex lens 3 and a second plano-convex lens 4. An aperture stop or diaphragm 5 is located between lenses 3 and 4. A further aperture stop or diaphragm 6 is located behind lens 4 in respect to the direction of the propagated light beam. Lenses 3 and 4 form a condenser. From the condenser, the light beam passes through a wedge-shaped sample holder 7 forming an optical cell made of transparent material such as glass, plastic or the like. A support, not shown, carries the sample holder in a manner to permit movement of the sample holder in a direction perpendicular to the light beam. This movement of the sample holder is in the direction of the wedge. A sample of the colloidal solution to undergo a measurement to determine the size of the colloid is contained in sample holder 7. The beam of light after passing through the sample holder propagates through an objective 8 and a prism 9. Dispersed light from the prism is projected onto an image screen 10.

Advantageously, a special prism is used to produce a wide-band spectrum of visible light. In a practical embodiment, the sample holder, made of plastic, has a length of 15 centimeters in the long direction of the wedge. The maximum thickness or width of the wedge is about 2 centimeters.

When a light beam is directed into a colloidal solution, the light is scattered and emerges sideways. The path of scattered light can be recognized due to the so-called Tyndall effect. It has now been discovered that the length of the Tyndall cone is dependent on the colloid size and on the concentration of the colloid in the solution. It follows from the above, that based on the length of the Tyndall cone at a known volume concentration of the colloidal solution, it is possible to determine the colloid or particle size.

To measure the Tyndall cone, the invention proceeds from the additional knowledge that the Tyndall cone ends at a location where the dispersion of light transmitted in the direction of propagation is dissipated by scattering. Consequently, the measuring procedure is carried out by moving the sample holder with differing layer thicknesses at right angles to the incident light beam until the emerging light beam contains only the longest wave part of the visible spectrum. That is, pure red light or monochromatic red light which is visible on the screen. When the end of the Tyndall cone with reference to the direction of incidence is precisely tangent to the rearward limit of the sample, only pure red light will be present on the screen. The length of the Tyndall cone "d" is determined by the measurement of distance of the light path through the solution sample. With each reduction in the layer or wedge thickness of the sample solution section in the holder light with a shorter wavelength will also appear on the screen. This also applies to self-colored particles, that is, to selective adsorption. The correctness of this statement can be verified by carrying out the measuring process with a solution containing colloid having several brightly colored pigments.

The length of the Tyndall cone can be changed at will by changing the concentration of the particles in the colloidal solution sample. A reduction in colloid concentration increases the distance between the particles of colloid and, as a result, a better transmittance of the light beam, that is, an increase in the length of the Tyndall cone.

The measurement of value "d" is used in the following equation:

$$r = \frac{1}{c \cdot d \cdot E_{(c)} \cdot n} \quad (1)$$

where r equals the radius of the particle in μm. In this equation, the value of the constant n is equal to $10^6/2$ mm and the concentration c is known.

The concentration factor $E_{(c)}$ depends on the concentration c of the colloidal solution being measured. Preferably, this concentration factor is determined in advance of the actual measuring procedure and concentration factors for colloidal solutions with different concentrations are listed in table form for convenient use.

With reference now to FIG. 2, the concentration factor is derived by using the volume of a sphere which is given by the following equation:

$$V_{sphere} = (4/3)\pi r^3 \quad (2)$$

and the volume of the cavity as shown in FIG. 2 is given by the equation:

$$V_{cavity} = 8(r+s)^3 - (4/3)\pi r^3 \quad (3)$$

where:
 r = radius of sphere, and
 s = ½(sphere-sphere distance).
It follows that the ratio of the sphere to cavity volumes is:

$$\frac{V_{sphere}}{V_{cavity}} = \frac{(4/3)\pi r^3}{8(r+s)^3 - (4/3)\pi r^3} \quad (4)$$

A synthetic resin dispersion solution with a 15% volume will serve as an example for the calculation.
 Specific gravity of the dispersion of plastic: $r = 1.1$.
 Sphere volume: 15:1.1 = 13.64%.
 Cavity volume: 100 − 13.64 = 86.36%.

$$\frac{13.64}{86.36} = \frac{(4/3)\pi r^3}{8(r+s)^3 - (4/3)\pi r^3}$$

r+s=1.5605r
s=1.5605r−r
s=0.56r
s=E·r where E is a proportionality factor
E=s·r=0.56.

According to Equation (4), it is a simple matter to calculate the proportionality factors for the solutions measured.

The computed particle radius r constitutes an equivalent sphere radius which is, however, generally employed as a basis for classifying disperse systems. A monodisperse system can be determined with a single measurement, while polydisperse systems can be classified by several measurements.

The following concentration ranges could be established for plastic dispersions in order to obtain a computable Tyndall cone:

|  | Range (in Vol. %) |
| --- | --- |
| Very fine dispersion | >10 |
| Fine to medium dispersion | 1–10 |
| Medium to coarse dispersion | 0.1–1 |
| Very coarse dispersion | 0.01–0.1 |

The above-described procedure is suitable for measuring all systems with particles in suspension, such as, for example, milk, pigments in the dispersed state, etc.

Although the invention has been shown in connection with a certain specific embodiment, it will be readily apparent to those skilled in the art that various changes in form and arrangement of parts may be made to suit requirements without departing from the spirit and scope of the invention.

We claim as our invention:

1. A method for determining the particle size of a colloidal solution, especially a synthetic resin dispersion, the method including the steps of: providing a colloidal solution sample with a thickness which varies in a given direction; directing a light beam to propagate through the colloidal solution sample in the direction normal to said given direction; causing the emerging light beam from the sample to undergo chromatic dispersion and to be incident onto an image screen; establishing, by a relative displacement between the light beam and the varying thickness of the colloidal solution sample, a sample position which results in only the long-wave part of the visible spectrum to appear on the screen; determining the thickness of the colloidal solution section which is traversed by the beam at said position; and, determining the particle size of the colloidal solution in accordance with the formula:

$$r = \frac{1}{c \cdot d \cdot E_{(c)} \cdot n}$$

where
r=radius of the particle (μm),
c=concentration of the colloidal solution in volume %,
d=thickness of measured colloidal solution sample section (mm),
$E_{(c)}$=concentration factor at concentration c, and
n=a constant.

2. The method according to claim 1 wherein said colloidal solution sample with a varying thickness is further defined to include a wedge-shaped sample of colloidal solution.

3. The method according to claim 2 wherein said step of establishing a measured colloidal solution sample section includes moving said wedge-shaped colloidal sample in the direction of the wedge and transversely to the direction at which said light beam is directed to propagate through the colloidal sample.

4. The method according to claim 1 wherein said long-wave part of the visible spectrum of dispersed light includes monochromatic red visible light.

5. The method according to claim 1 wherein said constant factor is further defined to equal $10^6/mm^2$.

6. Apparatus for determining the particle size of a colloidal solution, especially a synthetic resin dispersion, said apparatus including the combination of: a light source; a condenser to direct light from said light source for producing a narrow light beam; a wedge-shaped transparent sample holder for displacement in the direction of the wedge shape thereof within the path of the narrow light beam passed from said condenser, said sample holder being adapted to contain a sample of colloidal solution for the determination of the particle size thereof; lens means arranged for propagating light passed through said sample holder; means for dispersing light propagating from said lens means into the visible light spectrum; and an image screen for impingement by the dispersed light propagated from the dispersion means.

7. The apparatus according to claim 6 wherein said condenser includes two plano-convex lenses.

8. The apparatus according to claim 7 further including a diaphragm having an aperture arranged in the light path between said two plano-convex lenses.

9. The apparatus according to claims 6, 7 or 8 further including a diaphragm having an aperture arranged in the light path between said condenser and said wedge-shaped transparent sample holder.

10. The apparatus according to claim 6 further including a parabolic reflector means having a focal point receiving said light source.

* * * * *